US009561006B2

United States Patent
Elster et al.

(10) Patent No.: US 9,561,006 B2
(45) Date of Patent: Feb. 7, 2017

(54) BAYESIAN MODELING OF PRE-TRANSPLANT VARIABLES ACCURATELY PREDICTS KIDNEY GRAFT SURVIVAL

(71) Applicants: Eric A. Elster, Kensington, MD (US); Doug Tadaki, Frederick, MD (US); Trevor S. Brown, Gaithersburg, MD (US); Rahul Jindal, Silver Spring, MD (US)

(72) Inventors: Eric A. Elster, Kensington, MD (US); Doug Tadaki, Frederick, MD (US); Trevor S. Brown, Gaithersburg, MD (US); Rahul Jindal, Silver Spring, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 400 days.

(21) Appl. No.: 13/662,456

(22) Filed: Oct. 27, 2012

(65) Prior Publication Data

US 2014/0122382 A1 May 1, 2014
US 2016/0206249 A9 Jul. 21, 2016

Related U.S. Application Data

(63) Continuation-in-part of application No. 13/083,090, filed on Apr. 8, 2011, and a continuation-in-part of
(Continued)

(51) Int. Cl.
*G06F 15/18* (2006.01)
*A61B 5/00* (2006.01)
(Continued)

(52) U.S. Cl.
CPC ............ *A61B 5/7267* (2013.01); *A61B 5/201* (2013.01); *A61B 5/4848* (2013.01);
(Continued)

(58) Field of Classification Search
CPC .... G06F 19/345; G06F 19/24; G06F 19/3443; G06F 19/3431; G06N 99/005; G06N 5/04
See application file for complete search history.

(56) References Cited

U.S. PATENT DOCUMENTS 8,510,245 B2 * 8/2013 Stojadinovic et al. ......... 706/45
2002/0193667 A1 * 12/2002 McNair ............... G06F 19/3431
600/300
(Continued)

FOREIGN PATENT DOCUMENTS

WO    WO 2004015608 A2 *  2/2004
WO    WO 2009045115 A1 *  4/2009
(Continued)

OTHER PUBLICATIONS

Bayat et al, "Comparison of Bayesian Network and Decision Tree Methods for Predicting Access to the Renal Transplant Waiting List", 2009, Medical Information in a United and Healthy Europe, pp. 600-604.*
(Continued)

*Primary Examiner* — Paulinho E Smith
(74) *Attorney, Agent, or Firm* — Ning Yang; Albert M. Churill; Diane P. Tso

(57) ABSTRACT

An embodiment of the invention provides a method for determining a patient-specific probability of renal transplant survival. The method collects clinical parameters from a plurality of renal transplant donor and patient to create a training database. A fully unsupervised Bayesian Belief Network model is created using data from the training database; and, the fully unsupervised Bayesian Belief Network is validated. Clinical parameters are collected from an individual patient/donor; and, such clinical parameters are input into the fully unsupervised Bayesian Belief Network model via a graphical user interface. The patient-specific probability of disease is output from the fully unsupervised Bayesian Belief Network model and sent to the graphical user interface for use by a clinician in pre-operative organ matching. The fully unsupervised Bayesian Belief Network model is updated using the clinical parameters from the individual patient and the patient-specific probability of transplant survival.

5 Claims, 8 Drawing Sheets

Related U.S. Application Data application No. 13/123,406, filed on May 7, 2011, and a continuation-in-part of application No. 13/083,184, filed on Apr. 8, 2011, now Pat. No. 8,510,245.

(60) Provisional application No. 61/553,876, filed on Oct. 31, 2011.

(51) Int. Cl.
*A61B 5/20* (2006.01)
*G06F 19/00* (2011.01)

(52) U.S. Cl.
CPC .......... *A61B 5/7275* (2013.01); *G06F 19/322* (2013.01); *G06F 19/345* (2013.01); *G06F 19/3437* (2013.01)

(56) References Cited

U.S. PATENT DOCUMENTS

| | | | |
|---|---|---|---|
| 2005/0240544 A1* | 10/2005 | Kil et al. | 706/45 |
| 2007/0092888 A1* | 4/2007 | Diamond et al. | 435/6 |
| 2009/0275057 A1* | 11/2009 | Linke et al. | 435/7.23 |
| 2010/0057651 A1* | 3/2010 | Fung et al. | 706/12 |
| 2011/0289035 A1* | 11/2011 | Stojadinovic et al. | 706/45 |
| 2011/0289036 A1* | 11/2011 | Stojadinovic et al. | 706/45 |
| 2011/0295782 A1* | 12/2011 | Stojadinovic et al. | 706/12 |
| 2012/0065897 A1* | 3/2012 | Snider | C12Q 1/6883 702/19 |
| 2014/0122382 A1* | 5/2014 | Elster et al. | 706/12 |

FOREIGN PATENT DOCUMENTS

| | | |
|---|---|---|
| WO | WO 2010045463 A2 * | 4/2010 |
| WO | WO 2012162660 A2 * | 11/2012 |

OTHER PUBLICATIONS

Brown et al., "Bayesian Modeling of Pretransplant Variables Accurately Predicts Kidney Graft Survival", Dec. 5, 2012, American Journal of Nephrology, pp. 561-569.*

Stevens et al, "Bayesian Modeling of the United States Renal Data System Pre-Transplant Variables Accurately Predicts Graft Survival", Aug. 18, 2010, pp. 1.*

Hornberger et al., "Deciding Eligibility for Transplantation When a Donor Kidney Becomes Available", Jun. 1997, Society of Medical Decision Making, vol. 17/No. 2, pp. 160-170.*

Stojadinovic et all, "Development of a Clinical Decision Model for Thyroid Nodules", Aug. 10, 2009, BMC Surgery, vol. 9 No. 12, pp. 1-11.*

Rose et al., "A Dynamic Bayesian Network for Handling Uncertainity in a Decision Support System Adapted to Monitoring of Patients Treated by Hemodialysis", Nov. 16, 2005, Tools with Artificial Intelligence, pp. 1-5.*

Hariharan et al, "Improved Graft Survival After Renal Transplantation in the United States, 1988 to 1996", Mar. 2, 2000, Massachusetts Medical Society, vol. 342 No. 9, pp. 605-614.*

Russell et al, "Prediction of Renal Transplant Survival from Early Postopertiave Radioisotope Studies", Aug. 2000, Journal of Nuclear Medicine, vol. 41 No. 8, pp. 1332-1336.*

Prommool et al., "Time Dependency of Factors Affecting Renal Allograft Survival", 2000, Journal of American Society of Nephrology, vol. 11, pp. 565-573.*

* cited by examiner ns and distribution. (http://optn.transplant.hrsa-.gov/policiesAndBylaws/policies.asp). For example, in kidney transplantation cases, the matching system allocates organs based on time on list, human leukocyte antigen (HLA A locus, B locus and DR locus) matching, and whether recipient is suitable for an extended criteria donor (ECD) kidney. However, the tools currently used to make final allocation decisions are inadequate and subjective, which may result in sub-optimal graft survival. Acute rejection of the graft by the host's immune system remains an unsolved problem in allograft organ transplant. Immunosuppressive drugs are used to help to prevent and manage acute rejection episodes in many situations.

BAYESIAN MODELING OF PRE-TRANSPLANT VARIABLES ACCURATELY PREDICTS KIDNEY GRAFT SURVIVAL

I. CROSS-REFERENCE TO RELATED APPLICATIONS

This application claims the benefit of U.S. Patent Application No. 61/553,876 filed on Oct. 31, 2011, and is related to U.S. patent application Ser. No. 13/083,090 filed on Apr. 8, 2011, U.S. patent application Ser. No. 13/123,406 filed May 7, 2011 and U.S. patent application Ser. No. 13/083,184 filed on Apr. 8, 2011, which claimed the benefit of U.S. Patent Application No. 61/105,786 filed on Oct. 15, 2008, and U.S. Patent Application No. 61/166,245 filed on Apr. 2, 2009, which are hereby incorporated by reference.

II. FIELD OF THE INVENTION

The present invention relates to a model for providing patient-specific prognosis of disease or a medical treatment using clinical data. More particularly, the present invention relates to a fully unsupervised, machine-learned, cross-validated, dynamic Bayesian Belief Network model that utilizes clinical parameters for a determination of patient-specific probability of organ transplant.

III. BACKGROUND OF THE INVENTION

Within this application several publications are referenced by Arabic numerals within brackets. Full citations for these and other publications may be found at the end of the specification immediately preceding the claims. The disclosures of all these publications in their entireties are hereby expressly incorporated by reference into the present application for the purposes of indicating the background of the present invention and illustrating the state of the art.

An organ transplant surgery replaces a failing organ with a healthy organ. The success rates of transplant surgery have improved remarkably from its start, but growing shortages exist in the supply of organs and tissues available for transplantation. Organs and tissues that are transplanted within the same person's body are called autografts. Transplants that are performed between two subjects of the same species are called allografts. Allografts can either be from a living or cadaveric source.

The immune system is capable of discerning a cell as being 'self' or 'non-self' according to that cell's serotype. In humans, that serotype is largely determined by human leukocyte antigen (HLA), the human version of the major histocompatibility complex. Cells determined to be non-self are usually recognized by the immune system as foreign, resulting in an immune response. Serotypes differ widely between individuals. Therefore, if organ from one human are introduced into another human, the organ is oftentimes determined to be non-self because it do not match the self-serotype, and rejected by the recipient's immune system. Critical decisions must be made prior to organ transplantation to appropriately match donors and recipients.

In some situation, this rejection can be reduced by serotyping both recipient and potential donors to determine the closest HLA match. The United Network for Organ Sharing (UNOS) facilitates organ sharing for transplantation using policies developed by a committee of experts, and approved by the Secretary of Health and Human Services. These policies define the criteria by organ type for organ matching, procurement, and distribution. (http://optn.transplant.hrsa-.gov/policiesAndBylaws/policies.asp). For example, in kidney transplantation cases, the matching system allocates organs based on time on list, human leukocyte antigen (HLA A locus, B locus and DR locus) matching, and whether recipient is suitable for an extended criteria donor (ECD) kidney. However, the tools currently used to make final allocation decisions are inadequate and subjective, which may result in sub-optimal graft survival. Acute rejection of the graft by the host's immune system remains an unsolved problem in allograft organ transplant. Immunosuppressive drugs are used to help to prevent and manage acute rejection episodes in many situations.

However, as in the case of kidney transplantation, the expansion of the wait list far exceeds the number of available donor organs, contributing to the stress on the allocation system. In 2007, approximately 72,000 patients were listed with the United Network for Organ Sharing (UNOS), with only 17,513 receiving transplants, which was a 3% decrease over the previous year. Of those patients transplanted with deceased-donor grafts, approximately 10% of the grafts will fail in the first year with an additional 32% failing at five years and 61% at 10 years, which would return those patients to the wait list. In an effort to bridge this gap, medical professionals are relying on extended criteria donors (ECD) as well as donation after cardiac death (DCD). With the use of a greater number of these grafts, the ability to accurately predict graft failure becomes increasingly critical to maximize donation to the most suitable recipient and to minimize the flow of patients returning to the already burdened wait list. This application describes an objective tool that transplant surgeon may use for pairing donor organs with appropriate recipients to optimize outcomes.

As evidence-based medicine is becoming the standard of care, clinicians look towards prognostic tools to assist in decision making. [3] Machine learning can enable the development of a predictive model that incorporates multiple variables for a systems approach to organ allocation. Nomograms, neural networks, and decision trees have become popular methods for creating more objective ways to predict transplant outcomes [3, 5, 9-11]. While there are several publications on various models to predict allograft survival, these models rely on either both pre- and post-operative variables, or use only a handful of pre-operative variables for model functionality. Some of the models including nomograms, neural networks and tree-modeling offer positive predictive values for graft survival of 43.5%, 82.1% and 76%. [3-5] However, these models have not yet been implemented routinely in clinical setting.

Bayesian statistics is well suited to the analysis of large numbers of variables to predict outcomes. Originally developed in the 18th century, advances in computing power have made it practical today. Bayesian methodology has been used to predict survival in liver transplant patients, whereby using pre-transplant variables, the authors were able to predict 90-day survival with a positive predictive value (PPV) of 91% and an area under the curve (AUC) of 0.681. [6] The Bayesian modeling approach has not yet been applied to outcome prediction in renal allograft surgeries. Unlike traditional or frequentist statistical methods, Bayesian statistics lends itself to use with large databases, can tolerate missing values and incomplete variables, and can graphically describe the probability distributions of outcomes [7]. In other words, this type of statistical analysis allows for the use of an unlimited number of variables, and not only shows the relationship between each variable and the targeted outcome, but also the contribution of inter-variable relationships to the probability of each outcome.

This disclosure describes a machine-learning tool to generate a minimized Bayesian network that accurately predicts graft failure one and three years after transplantation based solely on pre-operative variables.

IV. SUMMARY OF THE INVENTION

An embodiment of the invention provides a highly predictive clinical decision support tool to assist physicians in rendering personalized organ matching and care decisions to improve graft survival. For instance, in at least one embodiment, a Bayesian Belief Network model is trained using a machine learning algorithm applied to large specific patient study population with pre-transplant variables. A broad statistically validated network structure of multiple clinical variables provides a universal method to produce individual prediction on transplant outcome (graft survival). This predictive risk assessment tool refines clinical decision making using multiple available parameters as well as partial information by providing case-specific risk scores in an operationally computational manner. The risk assessment tool and predictive model is updated continuously to include new clinical, treatment, and outcome information in order to expand its decision support capability. The dynamic, quantitative case-specific predictions made by the predictive model allow the clinical decision support tool to be adapted to the specific needs and capabilities of a given medical clinic. Given the following enabling description of the drawings, the apparatus should become evident to a person of ordinary skill in the art.

V. BRIEF DESCRIPTION OF THE DRAWINGS

The present invention is described with reference to the accompanying drawings. In the drawings, like reference numbers indicate identical or functionally similar elements.

Figure 5:
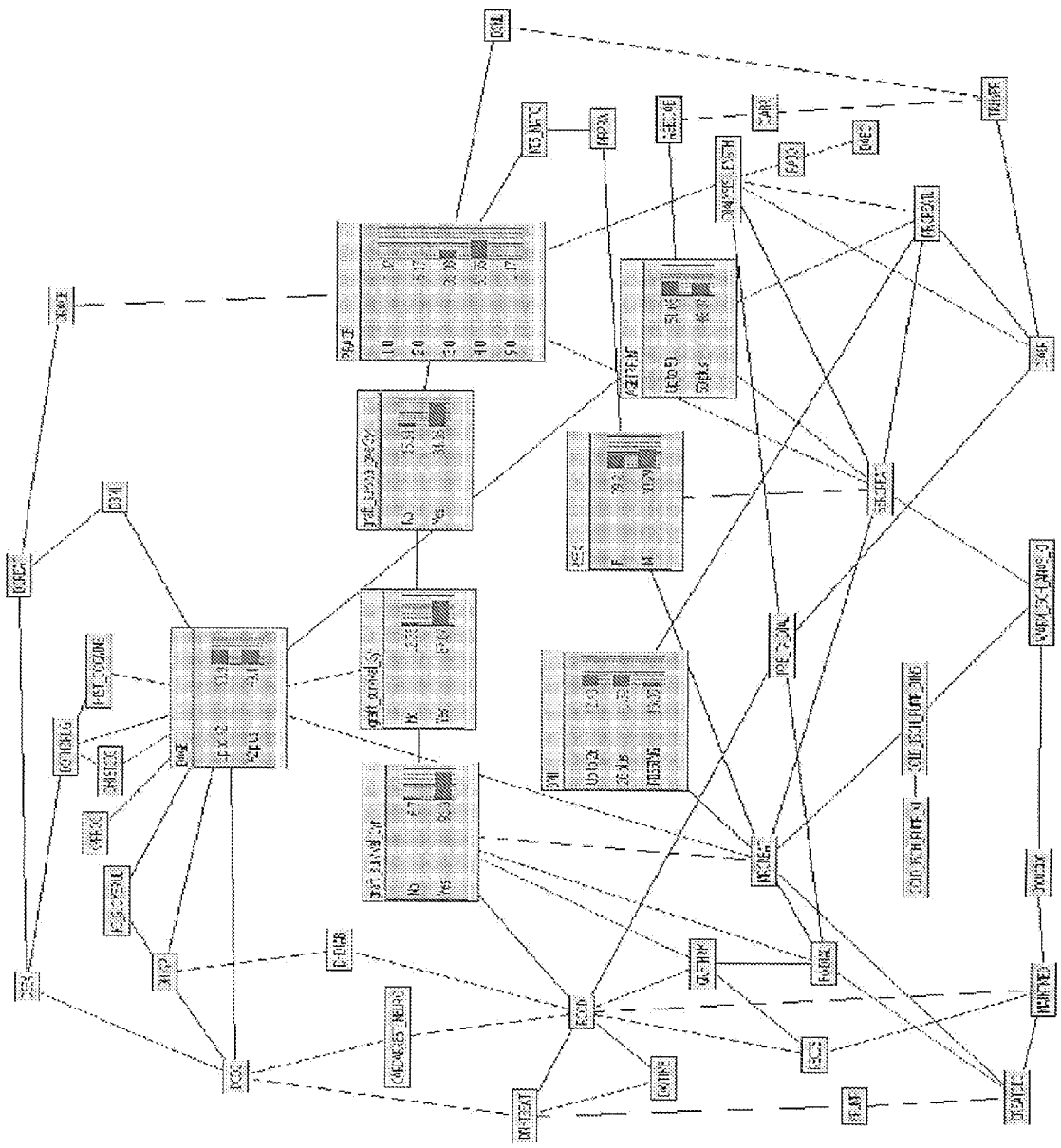

FIG. 5 illustrates a process for implementing the system according to an embodiment of the invention. Each box is a node and contains the probability distribution of a particular variable (see Table 2). Lines indicate the connectivity of the conditional dependences of these distributions. Post-transplant variables were ignored when calculating the predictions described in the text.

Figure 6:
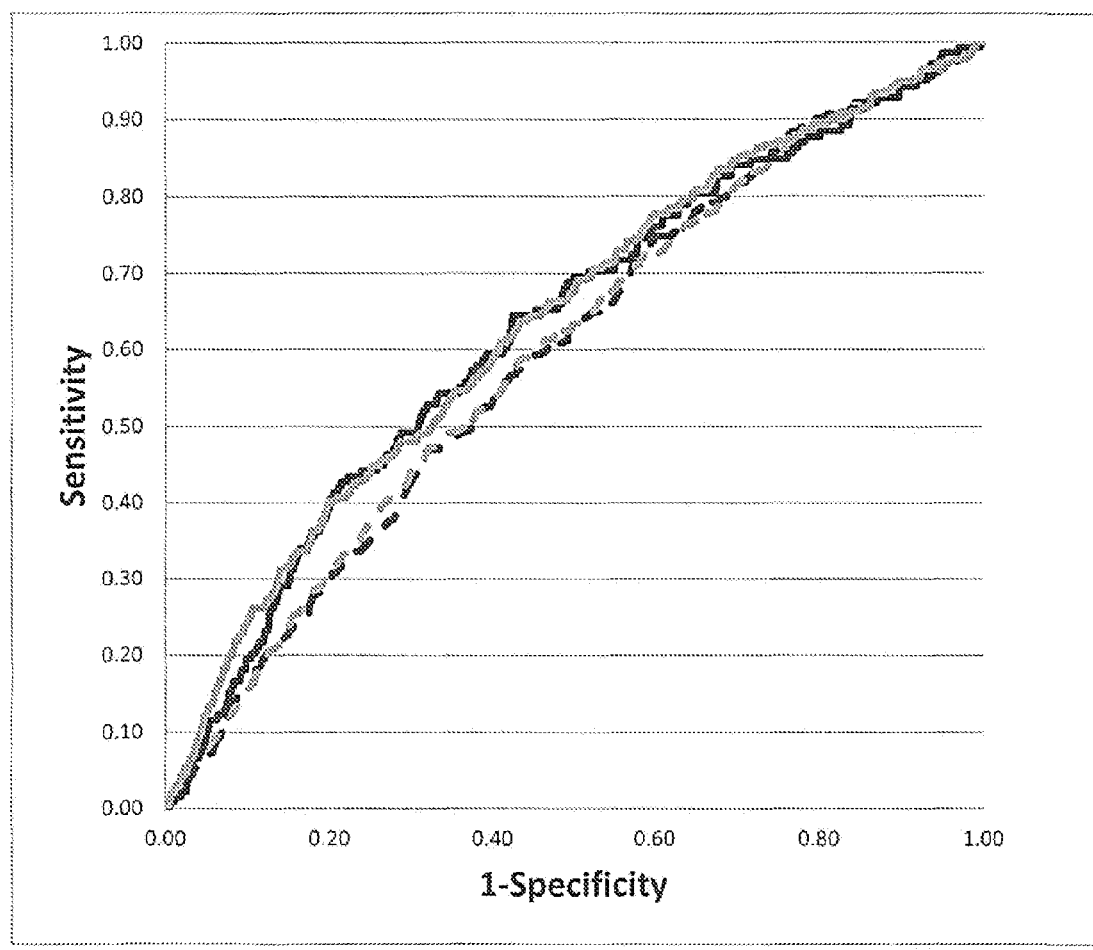

FIG. 6 illustrates ROC curves for external and internal model validations. The internal cross-validations (dashed lines) are shown overlaid with external validations (solid lines) for predictions of graft failure within one year (black) or three years (gray) to illustrate the similarity between the robustness of the model and its accuracy.

Figure 7:
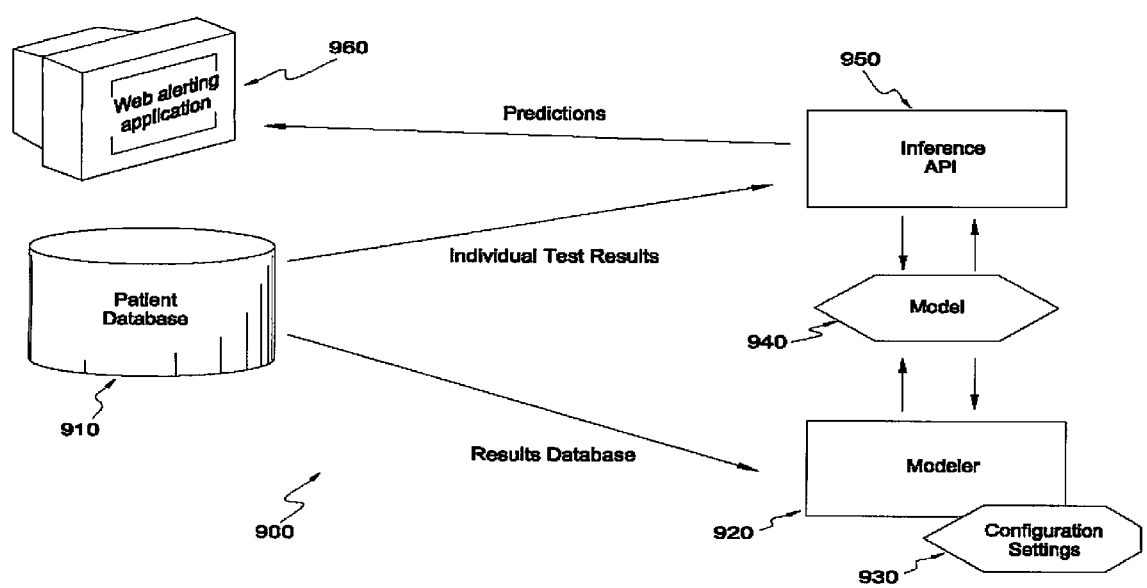
Figure 8:
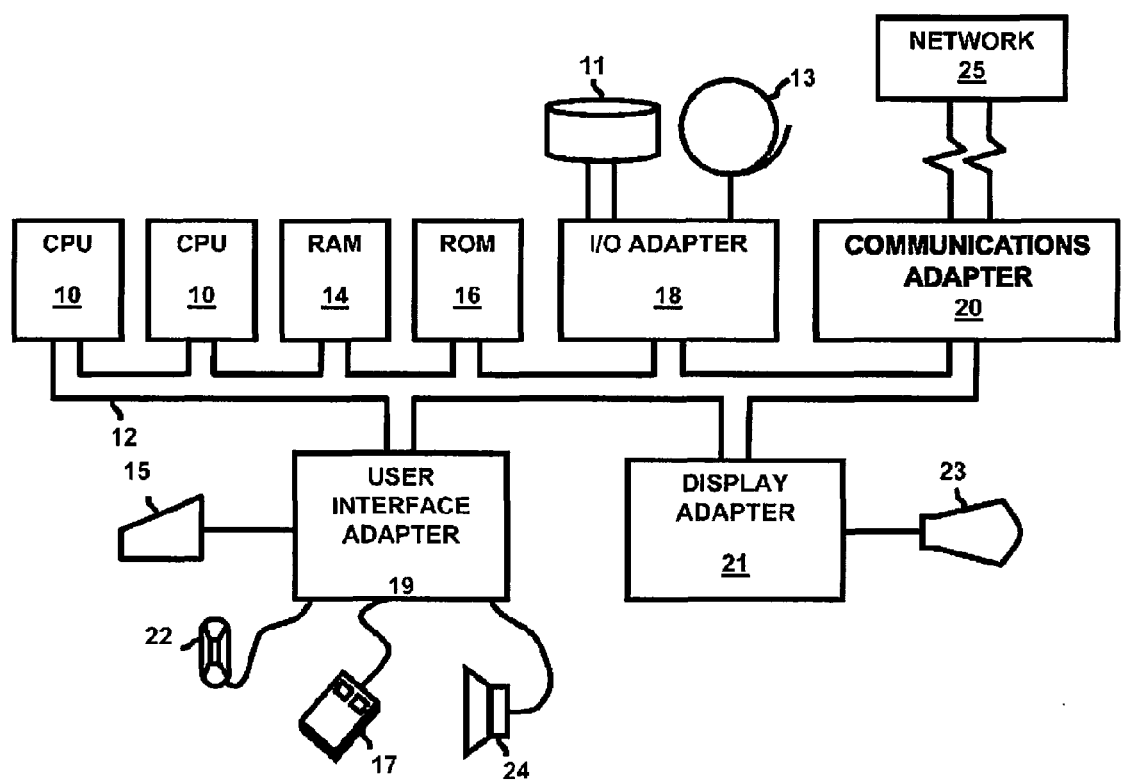

FIG. 7 illustrates a system for pre-operatively determining a patient-specific probability of graft survival according to an embodiment of the invention;

FIG. 8 illustrates a program storage device according to an embodiment of the invention.

VI. DETAILED DESCRIPTION OF THE DRAWINGS

Figure 1:
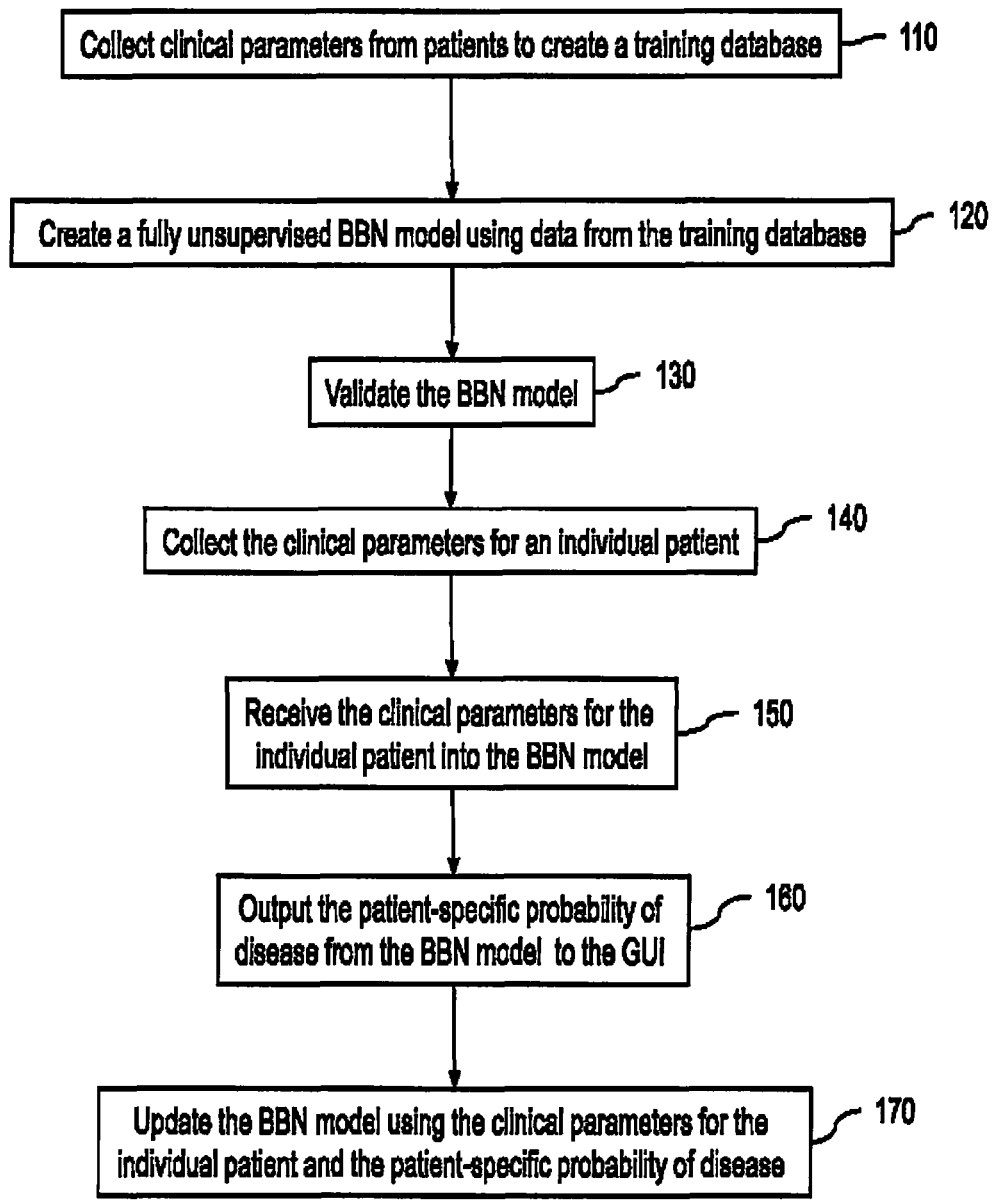
FIG. 1 is a flow diagram illustrating a method for pre-operatively determining a patient-specific probability of a disease or medical treatment according to an embodiment of the invention.

FIG. 1 provides a general overview of a method for pre-operatively determining a patient-specific probability of disease (e.g., malignancy in a thyroid nodule, graft survival, wound healing, and breast cancer) according to an embodiment of the invention. As described below, a fully unsupervised machine-learned Bayesian Belief Network model (referred to herein as the "BBN-ML") is created, updated, and deployed without human-developed decision support rules. A machine learning algorithm allows the BBN-ML to learn dynamically from data that resides in a data warehouse. The machine learning algorithm automatically detects and promotes significant relationships between variables without the need for human interaction. This allows for the processing of vast amounts of complex data quickly and easily into a tractable Bayesian network. The structure of the network provides the user with immediate knowledge about the nature of the problem set and the relative significance of variables to the outcome of interest. By inputting current knowledge into the BBN-ML, the user obtains a probability of outcome and relative risk in real-time.

The method collects clinical parameters from patients to create a training database (110). As described more fully below, examples of the clinical parameters include but not limited to a plurality of patient age/blood type/body mass index, donor age/BMI/blood type/gender, pre-operative assessment, Serum Creatinine of Cadaveric Donor, cause of death of Cadaveric Donor, length of time on dialysis, drug/cigarette use and/or history of diabetes or hypertension. Although in some embodiments, not all of the example clinical parameters are used in a particular BBN-ML A fully unsupervised Bayesian Belief Network model is created using data from the training database (120); and, the BBN-ML is validated (130). In at least one embodiment, the structure of the BBN-ML is a directed acyclic graph that is learned natively from prior probabilities resident in the training database. Each node in the directed acyclic graph represents a clinical parameter and includes two or more bins. Each bin represents a value range for the clinical parameter (e.g., bin 1: gene expression level less than or equal to 1.0; bin 2: gene expression level greater than 1.0). As described below, a node can be created such that each bin in the node includes an equal number of data points. For example, the value ranges of bins 1-3 can be created such that 33% of the training population is in each bin. In at least one embodiment, cross-validation is performed, wherein the data is randomized into groups of matched training and test data, a classifier is trained on each of the training sets created in the data preparation step using the same data discretization and modeling parameters. Then each corresponding test set is used to create a set of case-specific predictions. A Receiver-Operating Characteristic (ROC) curve is plotted for each test exercise to estimate model robustness and classification accuracy. Upon completion, the best model structure is documented in, for example, XML format for deployment as the BBN-ML. In at least one embodiment, the relevant learning parameter and modeling log files are stored if future audits are performed.

The method in at least one embodiment collects the clinical parameters from an individual patient (140), which is received into the BBN-ML (150). The patient-specific probability of surgical success is output from the BBN-ML to a graphical user interface for use by a clinician in pre-operative planning (160). As described more fully below, the Bayesian models are in an interactive format such that a clinician can select an outcome or relative clinical variable by clicking on the graphical user interface and observing corresponding changes to the probability distribution of the remaining variables. The graphical user interface is also used to enter current, patient-specific data and receive an evidence-based prediction of diagnosis (e.g., transplant survival in 1 to 3 years), thus enabling patient-risk stratification and clinical decision.

Figure 2:
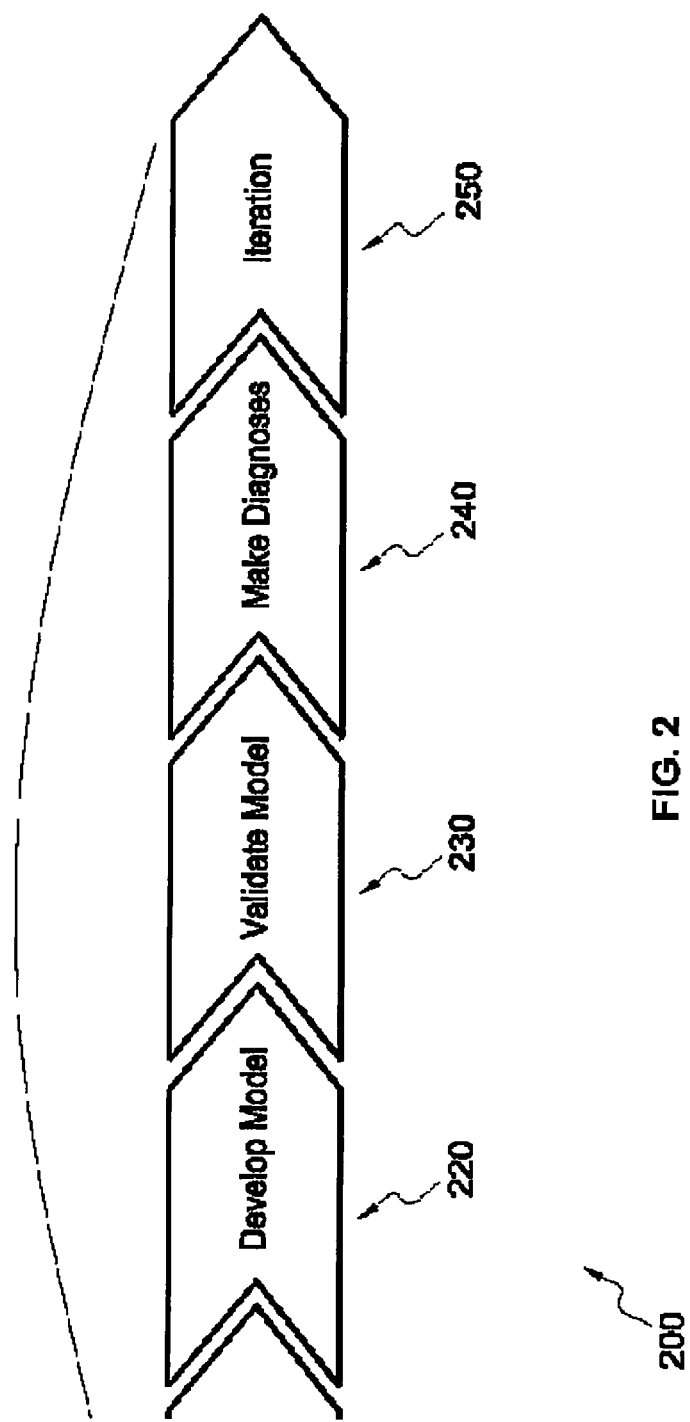
FIG. 2 illustrates a process of model development and deployment according to an embodiment of the invention.

The method updates the BBN-ML using the clinical parameters from the individual patient and the patient-specific probability of transplant graft survival (170). As illustrated in FIG. 2, according to at least one embodiment, the ongoing process of model development and deployment 200 is one of data collection 210, model development 220, model validation 230, model deployment (i.e., prognosis/prediction) 240, and iteration 250. This process is not static; it includes constant update, validation, and improvement. As new data is collected, models are updated and QC/QA documented.

Figure 3:
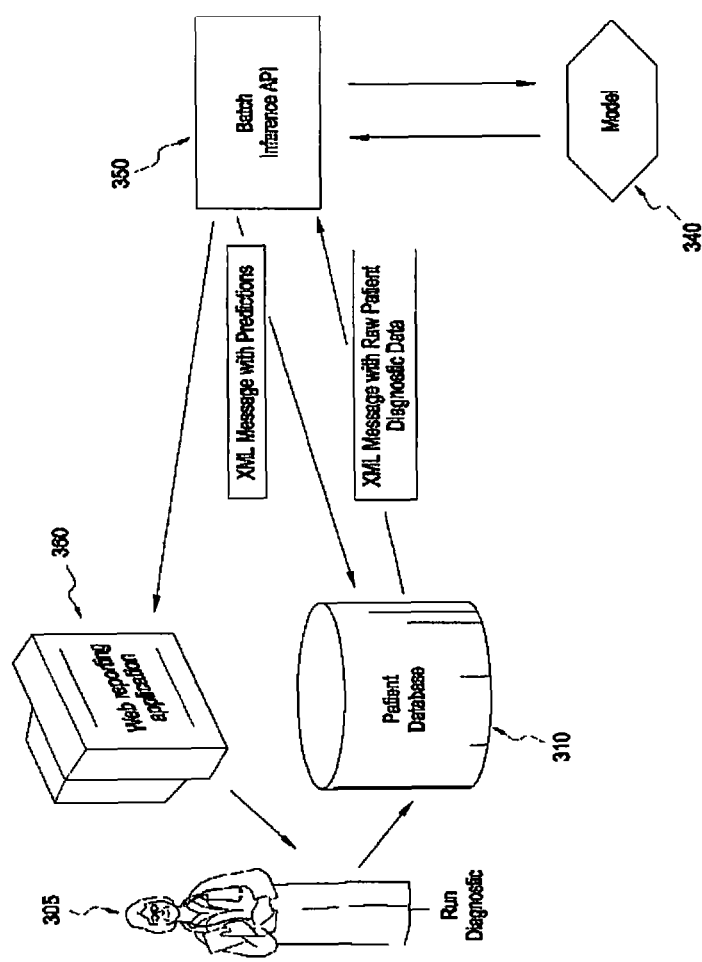
FIG. 3 illustrates a process for implementing the system according to an embodiment of the invention.
Figure 4:
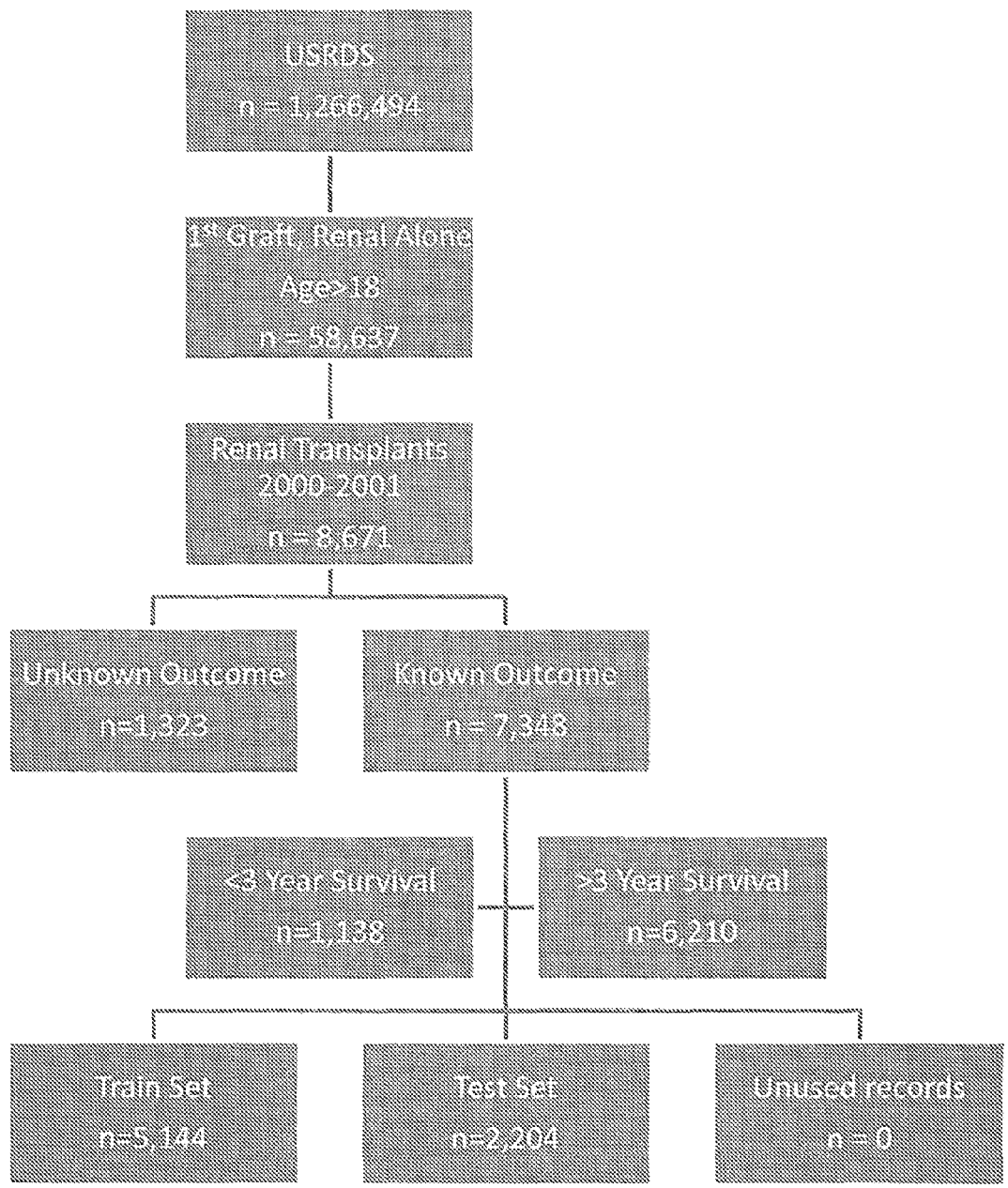
FIG. 4 illustrates cohort selection scheme for model construction and validation. The number of records (n) remaining after each step of the selection process based on our inclusion criteria is shown.

FIG. 3 illustrates a process flow for implementing a system for predicting a patient-specific probability of renal graft survival according to an embodiment of the invention. A clinician 310 runs diagnostic test(s) on a patient/donor (organ); and, results clinical data are written to a patient database 320 (also referred to herein as a "data warehouse" or "training database"). The database 320 sends, for example, an XML message with raw patient diagnostic data as well as donor (organ) data to a batch inference application programming interface (API) 330. The batch inference API 330 communicates with a model 340 (also referred to herein as the "BBN-ML") and receives a patient-specific prediction. The batch inference API 330 sends XML messages with the patient-specific prediction to the patient database 320 and a graphical user interface 350.

The following description provides example of using the systems and methodologies of the embodiments of the invention for predicting renal graft survival using pre-operative variables. Data used for model building was obtained from the USRDS database (2004).

A total of 1,266,494 cases were screened for data analysis (SPSS 16, SPSS Inc., Chicago, Ill.). Data was curated for accuracy and completeness. The Cohort selection scheme for model construction and validation is shown in Table 1. Inclusion criteria were first-time graft, 18 years of age or older and deceased-donor kidney-only recipient. The cohort was further narrowed by selecting transplants performed between 2000-2001, as this time period reflects current medication practices, and allows for follow-up. All cases in which outcome was unable to be determined were removed. Thus, 7,418 patients remained, of which 7,000 were randomly selected for model construction and validation. There were a total of 793 pre- and post-transplant variables extracted from the database, which were ultimately narrowed to 52 variables based on clinical expertise, global modeling, and excluding those variables collected during follow-up appointments that did not directly describe outcome. This process minimizes the complexity of the model and elucidates the value of variables that power outcome prediction. However, it may also eliminate variables previously considered individually associated with graft survival.

TABLE 1

Characteristics of the Study population

| | Donors | | Recipients | |
|---|---|---|---|---|
| | Train (n = 5,144) | Test (n = 2,204) | Train (n = 5,144) | Test (n = 2,204) |
| Age range (%) | | | | |
| 18-35 | 33.6 | 32.3 | 14.8 | 13.7 |
| 35-50 | 36.6 | 38.1 | 37.0 | 37.3 |
| >50 | 29.8 | 29.6 | 48.2 | 49.0 |
| Gender (%) | | | | |
| Male | 57.2 | 58.0 | 60.8 | 59.8 |
| Female | 42.8 | 42.0 | 39.2 | 40.2 |
| Race (%) | | | | |
| Native American | 0.2 | 0.4 | 0.9 | 0.6 |
| Asian | 2.0 | 2.5 | 5.0 | 4.2 |
| Black | 10.3 | 9.9 | 31.2 | 30.8 |
| White | 86.9 | 86.6 | 61.9 | 63.6 |
| Other | 0.5 | 0.6 | 1.0 | 0.8 |
| BMI categories (%) | | | | |
| 0-25 | 46.3 | 46.7 | 29.7 | 29.7 |
| 25-35 | 45.0 | 44.9 | 46.3 | 45.5 |
| >35 | 8.5 | 8.2 | 8.0 | 8.1 |
| Pre-transplant dialysis (%) | | | | |
| No | | | 7.6 | 8.2 |
| Unknown | | | 0.8 | 0.9 |
| Yes | | | 91.6 | 90.9 |
| Graft failure (%) | | | | |
| 1 y | | | 6.6 | 6.3 |
| 3 y | | | 12.3 | 11.6 |
| >3 y | | | 15.6 | 15.3 |

All data processing was done with either SPSS® (v. 16-18) or EXCEL® (2007, Microsoft Corp., Redmond, Wash.). Outcomes of interest were 1, 3, and >3 year survival. Graft survival was calculated as time from transplant date to graft failure date. In the absence of a graft failure date, surrogates for failure were used (a return to maintenance dialysis, a second transplant, or recipient date and cause of death. Grafts that did not fail within the confines of our dataset were given a survival length using their latest follow-up date as a report of minimum survival. If a patient did not have a follow-up date reported or was lost to follow-up without a report of graft failure, then that patient was removed from analysis.

FIG. 7 illustrates a system 900 for pre-operatively determining a patient-specific probability of renal transplant survival according to an embodiment of the invention. A patient database 910 includes individual patient records. This can either be a standalone database or an existing clinical information system, such as an electronic health record database. The system 900 uses patient data to train new iterations of the model 940 (also referred to herein as the "BBN-ML") and to make individual patient predictions. Machine learning software 920 is also used to retrain the model 940 with new data. The machine learning software 920 includes a configurations file 930, which contains the settings for learning. The model 940 is an XML model that specifies structure and joint probability distributions. The batch inference API 950 uses the model 940 and individual patient data from the patient database 910 to produce patient-specific predictions. A graphical user interface (GUI) 960 (e.g., web-based or client-server) receives the patient-specific predictions in the form of reports.

The current network model was constructed using a minimum description length (MDL) gain (a weighting of the MDL or the Bayesian information criterion that trades off goodness of fit for model complexity) of 0.5. An MDL gain of 1.0 leads to a relatively equal weighting of representation of the known data and complexity to yield a robust model. Continuous variables were divided into two bins based on equal areas under the distribution curves; use of three bins was also investigated and did not result in added benefit. Binning continuous variables, has the benefit of reducing 'noise' in the data, but also loses information. An additional bin was included for missing data where appropriate.

The network was queried to provide estimates for posterior probabilities given a priori knowledge, and the model accuracy was validated using data from 2,204 patients withheld from the initial training dataset. Probability of graft survival was calculated using only variables whose values could be known prior to transplantation and ignoring all post-transplant variables. Model performance was evaluated using receiver operator characteristic curves (ROC). The area under the curve (AUC) is calculated as a measure of classification accuracy with 0.5 representing random chance, i.e. the model is right just as often as it is wrong, and 1.0 (or 0.0) indicating perfect classification of both the positive and negative outcomes.

A 10-fold internal cross-validation was used to assess robustness. It was then externally validated with an additional 2204 patients from the same time period to evaluate functionality. Finally, an additional cohort of patients randomly selected from the years 1997, 2002, and 2003, and meeting the same selection criteria as the model training cohort, were used as a test set to evaluate model robustness with respect to transplant year.

As a demonstration of utility, the model was used to estimate the number of grafts that could have been reallocated for improved, predicted graft survival. Two Organ Procurement Transplantation Networks (OPTN)—OPTN 2 (Washington D.C., New Jersey, Maryland, West Virginia, and Pennsylvania) with a long wait time and OPTN 6 (Hawaii, Washington, Oregon, Alaska, Montana, and Idaho) with a short wait time—were evaluated. As a matter of reference, based on OPTN data as of Apr. 29, 2011 for kidney registrations listed 1999-2004, OPTN 2 had a median waiting time of 1,357 days (Caucasian recipients; 2003-2004) and OPTN 6 had a median waiting time of 831 days (via optn.transplant.hrsa.gov on May 5, 2011).

Finally, the donor information from a graft that failed within the first year was applied to other recipients in this same two-year cohort to demonstrate how the model may be used as an allocation tool.

The donor and recipient characteristics for key variables from the 5000-patient model training dataset and the 2000-patient external validation dataset were compared. Both populations were well matched for donor and recipient age, gender, race, and BMI ($p>0.05$). The recipients were well matched for time on dialysis, and graft survival ($p>0.05$; Table 1). The internal, 10-fold cross-validation confirmed model robustness, as measured by area under the curve (AUC), for both one-year and three-year graft failure (0.59 and 0.60, respectively). This exercise yielded a sensitivity and specificity for graft failure of 24.3% and 83.4% respectively one year and 30.6% and 80.2% respectively three years post-transplantation using a threshold of 8.35% (one-year failure) or 14.3% (three-year failure) probability for a positive test.

The external validation also demonstrated predictive accuracy for identifying one-year and three-year graft failure (AUC 0.63 and 0.63). The embodiment model successfully identified 55 of the 138 grafts that failed within one year following current allocation practices. ROC curves are shown superimposed in FIG. 6. Using the thresholds mentioned above for a positive test for graft failure, our model had a sensitivity of 39.9% and specificity of 79.9%. This was maintained for three-year graft failure with a sensitivity of 39.8%, specificity of 80.2%. Positive and Negative predictive values differed greatly between a balanced test cohort, which has an equal number of cases in each graft failure class, and one that is representative of the incidence rate, but is over-representative of graft survival (data not shown). The latter was pursued in order to present the most conservative model; one that considers the largest cohort available and demonstrates the 'promise' of a machine learning approach to donor-recipient matching.

BBN demonstrated that recipient BMI, gender, race, and donor age drive predictive outcome. The Bayesian Belief Network (BBN) consisted of 48 nodes, with 37 nodes representing pre-transplant variables, 12 representing post-op variables, and 3 nodes representing outcomes of 1, 3, and >3 y survival (Table 2; FIG. 5).

TABLE 2

USRDS Derived Donor and Recipient Variables

| Abbreviation | Definition |
| --- | --- |
| AGEDIAB | Age of Diabetes Onset |
| AGETRPLNT | Recipient age at time of transplant in years |
| BMI | Body Mass Index |
| CARDARREST_NEURO | Cardiac arrest since neurological event that led to declaration of brain death |
| COLD_ISCH_PUMP_BINS | Cold_isch_pump_ki (combined right and left kidneys) |
| COLD_ISCH_PUMP_KI | Combined COLD_ISCH_PUMP |
| CREATDEC | Creatinine decline by 0.25 or more in first 24 hour |
| DABO | Donor Blood Type |
| DAGE | Donor Age |
| DBMI | BMI of Cadaveric Donor |
| DCOD | Cadaveric Donor Cause of Death |
| DCREAT | Serum Creatinine of Cadaveric Donor |
| DGNL | Primary Diagnosis |
| DHDIAB | History of Diabetes (Cadaveric Donor) |
| DHHYP | History of Hypertension (Cadaveric Donor) |
| DHISTCIG | Cigarette Use (>20 pack years) - Ever (Cadaveric Donor) |
| DIABR | Patient Diabetes |
| DIALR | Dialysis at Listing (Recipient) |
| DIALYSIS_LENGTH | Length of time on dialysis pre-transplant in days |

TABLE 2-continued

USRDS Derived Donor and Recipient Variables

| Abbreviation | Definition |
| --- | --- |
| DNHTBEAT | Was this a DCD donor (non - heartbeating) |
| DOTHDRUG | Other Drug Use (non - IV) (Cadaveric Donor) |
| DRACE | Donor Race |
| DSEX | Donor Gender |
| DWTIME | Estimated Warm Ischemic Time |
| FWDIAL | Patient need dialysis within first week |
| graft_survival_1yr | Graft survival at least 1 year |
| graft_survival_3yr | Graft survival at least 3 year |
| graft_survival_over3yr | Graft survival more than 3 year |
| GRFTHRM | Graft thrombosis |
| HIST_COCAINE | Cocaine Use - Ever (Cadaveric Donor) |
| Induction | Induction medications combination |
| KPPROC | Procedure type |
| KPUMP | Pump (Combined Right and Left Kidney) |
| MAINTMED | Are any medicines given currently for maintenance or anti-rejection? |
| MIS_MATC | CNT HLA A, B, DR MIS_MATCH (0-6) |
| MRCREAT | Most recent serum Creatinine prior to discharge |
| MRCREATL | Most recent absolute Creatinine at listing |
| MRPRA | Most Recent USRDS PRA(%) |
| PRE_TX_DIAL | pre_tx_dial |
| RABO | Recipient Blood Type |
| RECDS | Recurrent disease |
| RRACE | Patient Race (Recipient) |
| RSEX | Gender |
| SERCREAT | Serum Creatinine at time of transplant |
| TRHYPR | Drug treated systemic hypertension at listing (Recipient) |
| WARM_ISCH_ANAS_KI | Warm ischemia anastomotic time in minutes (combined right and left kidneys) |

Note,
these variable definitions are based on definitions supplied by the United States Renal Data System (USRDS) via the 2007 ADR Edition of the Researcher's Guide to the USRDS Database.

The model showed recipient BMI, gender, race, and donor age to be the pre-transplant variables with strongest association with survival as illustrated by being primary or secondary nodes of the graft survival nodes in the model (FIG. 5). Of those nodes, one (donor age) was classified as a parent of an outcome node, while the remaining nodes were classified as having a shared child with or are grandparents or children of the outcome nodes. Although time on dialysis (a surrogate for time on list) and HLA-matching are both associated with graft survival, as can be seen in the network, they are not as closely related to outcome as the aforementioned variables (FIG. 5).

Model performance is affected by sampling time. The effect of sampling timeframe on model performance was tested using data from 4422 patients from 1997, 3615 from 2002, and 423 from 2003, which were the total number of records meeting the selection criterion as per the 2000-2001 cohort. The performance as measured by AUC was 0.59 for 1997, 0.597 for 2002, and 0.50 for 2003 for 1-year failure. The predictive performance for 3-year failure for 1997 was 0.59 and for 2002 was 0.60 as measured by AUC. Three year survival was not evaluated for 2003 as the USRDS data obtained for our investigation concluded with January 2005.

The model was applied to two OPTNs to demonstrate the potential for region-specific graft recovery. For the years 2000 and 2001 in OPTN 2 (New Jersey, Pennsylvania, Maryland, District of Columbia, Delaware, and West Virginia), 890 transplants meeting the selection criteria were performed. Of those, 77 failed within the first year; using the same probability thresholds as the validation exercises, the model predicted 37 of those as failures with a sensitivity of 48.1% and specificity of 70.2%. This equates to a potential 4% graft re-allocation. One hundred and twenty-four grafts failed in the first three years. The model predicted 60 of those failures with a sensitivity of 48.4% and specificity of 70.5%. When applied to OPTN 6 (Washington, Oregon, Idaho, Montana, and Hawaii), with a shorter wait time the results were similar. Of the 279 grafts in this cohort transplanted in 2000 or 2001, 19 grafts failed in the first year. This model predicted 4 of those failures, which would suggest that an additional 1.43% of available organs (or 21.1% of those failures) should be re-allocated to another candidate recipient.

To demonstrate this, a patient whose graft failed in the first year post-transplant was selected randomly from the OPTN 2 data. The donor information was then applied to all recipients in the above described cohort (n=890). Seventy-seven grafts in this sub-cohort failed within the first year, thirty of which the model predicted would survive had that recipient received the example organ. Interestingly, this "re-allocation" was predicted to lead to three-year survival for twenty-five of these new donor-recipient pairs with probabilities ranging from 0.105 to 0.143 for graft failure. Additionally, 51% of the remaining 813 recipients, all of whose grafts survived the first year, were also predicted to have survived with the example organ with >0.916 probability.

With regard to three-year graft survival, the model identified 18 recipients whose graft survived longer than one year, but failed in less than three years, that might have survived greater than three years with a re-allocation of the example organ (<0.138 failure probability). The 47 failed allografts that were also classified as failures within the first year with this hypothetical donor continued to be identified as failures at three years. The remaining surviving grafts were predicted to have also survived with this organ.

This is the first study that uses BBN to predict outcomes in deceased kidney transplantation and places donor age as one of the most important pre-transplant predictors of outcome [14-16]. Recipient BMI, gender and race are also influential predictors of outcome in the model, while wait time and HLA-matching are shown to be much less associated with outcome. This is illustrated in the model graphic as donor age (DAGE) is a primary variable of, or shares an arc with, graft survival greater than three years (graft_survival_over3yr), while recipient gender (RSEX) and BMI (BMI) are secondary variables to a minimum of one year graft survival (graft_survival_1yr). The influence of combinations of these factors on one- and three-year outcome can be seen explicitly in Table 3.

TABLE 3

Inference Table of Variables of Interest and 1-year Graft Survival Probability

| [a]Probability of case | BMI | DAGE | RRACE | RSEX | [b]graft_survival_1yr | |
|---|---|---|---|---|---|---|
| | | | | | No | Yes |
| 0.10% | Up to 26 | Up to 42 | 1 | F | 5.5 | 94.5 |
| 0.09% | 26 plus | Up to 42 | 1 | F | 6.8 | 93.2 |
| 0.09% | Up to 26 | 42 plus | 1 | F | 11.2 | 88.8 |
| 0.09% | 26 plus | 42 plus | 1 | F | 13.5 | 86.5 |
| 0.46% | Up to 26 | Up to 42 | 2 | F | 2.4 | 97.6 |
| 0.41% | 26 plus | Up to 42 | 2 | F | 3 | 97 |
| 0.40% | Up to 26 | 42 plus | 2 | F | 5.1 | 94.9 |
| 0.38% | 26 plus | 42 plus | 2 | F | 6.2 | 93.8 |
| 2.60% | Up to 26 | Up to 42 | 3 | F | 5.5 | 94.5 |
| 2.32% | 26 plus | Up to 42 | 3 | F | 6.7 | 93.3 |
| 2.35% | Up to 26 | 42 plus | 3 | F | 11 | 89 |
| 2.28% | 26 plus | 42 plus | 3 | F | 13.1 | 86.9 |
| 5.77% | Up to 26 | Up to 42 | 4 | F | 3.3 | 96.7 |
| 5.19% | 26 plus | Up to 42 | 4 | F | 4.1 | 95.9 |
| 5.08% | Up to 26 | 42 plus | 4 | F | 6.9 | 93.1 |
| 4.94% | 26 plus | 42 plus | 4 | F | 8.5 | 91.5 |
| 0.11% | Up to 26 | Up to 42 | 9 | F | 3.2 | 96.8 |
| 0.10% | 26 plus | Up to 42 | 9 | F | 4 | 96 |
| 0.09% | Up to 26 | 42 plus | 9 | F | 6.8 | 93.2 |
| 0.09% | 26 plus | 42 plus | 9 | F | 8.3 | 91.7 |
| 0.12% | Up to 26 | Up to 42 | 1 | M | 6 | 94 |
| 0.12% | 26 plus | Up to 42 | 1 | M | 6.9 | 93.1 |
| 0.12% | Up to 26 | 42 plus | 1 | M | 11.1 | 88.9 |
| 0.13% | 26 plus | 42 plus | 1 | M | 12.5 | 87.5 |
| 0.69% | Up to 26 | Up to 42 | 2 | M | 2.5 | 97.5 |
| 0.67% | 26 plus | Up to 42 | 2 | M | 3 | 97 |
| 0.64% | Up to 26 | 42 plus | 2 | M | 5.1 | 94.9 |
| 0.67% | 26 plus | 42 plus | 2 | M | 5.8 | 94.2 |
| 4.13% | Up to 26 | Up to 42 | 3 | M | 5.8 | 94.2 |
| 4.00% | 26 plus | Up to 42 | 3 | M | 6.8 | 93.2 |
| 4.03% | Up to 26 | 42 plus | 3 | M | 11 | 89 |
| 4.23% | 26 plus | 42 plus | 3 | M | 12.4 | 87.6 |
| 7.88% | Up to 26 | Up to 42 | 4 | M | 3.6 | 96.4 |
| 7.67% | 26 plus | Up to 42 | 4 | M | 4.1 | 95.9 |
| 7.46% | Up to 26 | 42 plus | 4 | M | 6.9 | 93.1 |
| 7.85% | 26 plus | 42 plus | 4 | M | 7.9 | 92.1 |
| 0.15% | Up to 26 | Up to 42 | 9 | M | 3.5 | 96.5 |
| 0.15% | 26 plus | Up to 42 | 9 | M | 4.1 | 95.9 |
| 0.14% | Up to 26 | 42 plus | 9 | M | 6.8 | 93.2 |
| 0.15% | 26 plus | 42 plus | 9 | M | 7.7 | 92.3 |

Note:
Scenarios with "Missing" data have been omitted for clarity.
[a]The perecent of total cases (n = 5,144) with the particular combination of values indicated.
[b]The graft was maintained for at least one year (graft_survival_1yr).

BBN was able to weigh how each variable in the network, major or minor, influence each other to affect outcome, in contrast to other, more traditional nomograms. In essence, BBN takes raw data in the form of individual probability distributions and refines that into a fluid network that accurately predicts renal transplant outcomes.

This model accurately predicts those donor-recipient matches that will have a poor one-year outcome as illustrated by the sensitivity of 40%. Furthermore, for those donor-recipient pairs that were already a good match, the embodiment model did not overly predict them incorrectly as failures, as seen by the high specificity of 80%. In other words, the model would be able to reclaim or re-allocate two-fifth of the renal allografts that may have been lost in the first year due to a less than idea recipient selection. Another benefit of the Bayesian model is that, while individual variables such as recipient gender may not reliably predict outcome, these same variables populating a network can accurately predict graft outcomes.

While this model's performance decreases slightly with time-from-transplant, it maintains a high survival predictive value (>87%) as well as a high specificity (>77%). As the used threshold values that would provide for at least 40% identification of failed grafts, we interpret this as correctly predicting those grafts that would fail while not incorrectly classifying good matches as failures. Although not all of the grafts that failed were captured under the current allocation system, the identification of poor matches is improved by 40% for one-year and three-year failures, and potentially warrants re-allocation of the organ to another qualified recipient. Even though there is a low percent failure rate for cadaveric donor transplants within the first few years, avoid graft failure in an additional 40% of those that failed within the first year translates into ~500 additional grafts annually, and thus, a potentially significant reduction in the number of recipients returning to the wait list.

The practical effect of using the BBN as a decision making tool in renal allograft allocation may be multifold. Less organ waste and reduced cold ischemic times. Currently nearly 20% of all donor kidneys are discarded, the majority being of marginal quality [19]. However, with this model, the pre-transplant characteristics of the particular donor and the proposed recipients can be compared for a prediction of outcome. And, as this model can be deployed in XML format, a center could enter the known donor characteristics into a web-based interface and compare the risk of failure based on each prospective recipient's characteristics.

For example, with a kidney donation from a 44-year-old White male without a history of diabetes and with a BMI of 30, a 39-year-old White female without diabetes and with a BMI of 22 (each of these values, or evidence, is entered directly into the model) is associated with 83.45% probability of greater than 3 years graft survival. A 55-year-old Black male with non-insulin dependent diabetes and a BMI of 29 is associated with 74.67% probability. Finally, a 39-year-old Black female with non-insulin dependent diabetes and a BMI of 32 is associated with a 72.5% probability of graft survival over 3 years.

This model can be used to augment the current allocation system. The current UNOS system should continue to be used to generate the 'short list' of candidate recipients matching a particular donor organ. This model would then be applied as a "mathematical equation" that uses the donor's and recipients' information to determine which match would result in the longest-term outcome. The proposed method of matching may have the potential to save more than 40% of grafts that fail within their first year.

The invention can take the form of an entirely hardware embodiment or an embodiment containing both hardware and software elements. In at least one exemplary embodiment, the invention is implemented in a processor (or other computing device) loaded with software, which includes but is not limited to firmware, resident software, microcode, etc.

A representative hardware environment for practicing at least one embodiment of the invention is depicted in FIG. 8. This schematic drawing illustrates a hardware configuration of an information handling/computer system in accordance with at least one embodiment of the invention. The system includes at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

Computer program code for carrying out operations of the present invention may be written in a variety of computer programming languages. The program code may be executed entirely on at least one computing device (or processor), as a stand-alone software package, or it may be executed partly on one computing device and partly on a remote computer. In the latter scenario, the remote computer may be connected directly to the one computing device via a LAN or a WAN (for example, Intranet), or the connection may be made indirectly through an external computer (for example, through the Internet, a secure network, a sneaker net, or some combination of these).

It will be understood that each block of the flowchart illustrations and block diagrams and combinations of those blocks can be implemented by computer program instructions and/or means. These computer program instructions may be provided to a processor of a general purpose computer, special purpose computer, application specific integrated circuit (ASIC), or other programmable data processing apparatus to produce a machine, such that the instructions, which execute via the processor of the computer or other programmable data processing apparatus, create means for implementing the functions specified in the flowcharts or block diagrams.

The invention has industrial applicability to predict a patient-specific diagnosis of disease. The invention utilizes a fully unsupervised, cross-validated, and dynamic BBN-ML that utilizes clinical parameters for determining the patient-specific diagnosis, which can be utilized to alter or improve the patient's lifestyle or to adjust therapy in a proactive manner.

REFERENCES

1. Patel S, Cassuto J, Orloff M, Tsoulfas G, Zand M, Kashyap R, et al. Minimizing morbidity of organ donation: analysis of factors for perioperative complications after living-donor nephrectomy in the United States. Transplantation. 2008; 85(4): 561-5.
2. United States Renal Data System, Researcher's Guide to the USRDS Database, National Institutes of Health, National Institute of Diabetes and Digestive and Kidney Diseases, Bethesda, Md., 2007.
3. Akl A, Ismail A M, Ghoneim M. Prediction of Graft Survival of Living-Donor Kidney Transplantation: Nomograms or Artificial Neural Networks? Transplantation. 2008; 86(10): 1401-6.
4. Goldfarb-Rumyantzev A S, Scandling J D, Pappas L, Smout R, Horn S D. Prediction of 3-yr cadaveric graft survival based on pre-transplant variables in a large national dataset. Clinical Transplantation. 2003; 17(6): 485-97.
5. Krikov S, Khan A, Baird B C, Barenbaum L L, Leviatov A, Koford J K, et al. Predicting kidney transplant survival using tree-based modeling. ASAIO J. 2007; 53(5): 592-600.
6. Hoot N, Aronsky D. Using Bayesian networks to predict survival of liver transplant patients. AMIA Annu Symp. Proc. 2005: 345-9.
7. Grunkemeier G L, Payne N. Bayesian analysis: a new statistical paradigm for new technology. Ann Thorac Surg. 2002; 74(6): 1901-8.
8. Moraleda J, Stanford University. Dept. of Electrical Engineering. New algorithms, data structures, and user interfaces for machine learning of large datasets with applications [Thesis (PhD)]: Stanford University; 2004.
9. Brier M E, Ray P C, Klein J B. Prediction of delayed renal allograft function using an artificial neural network. Nephrol Dial Transplant. 2003; 18(12): 2655-9.
10. Lin R S, Horn S D, Hurdle J F, Goldfarb-Rumyantzev A S. Single and multiple time-point prediction models in kidney transplant outcomes. Journal of Biomedical Informatics. 2008; 41(6): 944-52.
11. Tiong H Y, Goldfarb D A, Kattan M W, Alster J M, Thuita L, Yu C, et al. Nomograms for predicting graft function and survival in living donor kidney transplantation based on the UNOS Registry. J. Urol. 2009; 181(3): 1248-55.
12. Collins M G, Chang S H, Russ G R, McDonald S P. Outcomes of Transplantation Using Kidneys From Donors Meeting Expanded Criteria in Australia and New Zealand, 1991 to 2005. Transplantation. 2009; 87(8): 1201-9.
13. Stratta R J, Sundberg A K, Rohr M S, Farney A C, Hartmann E L, Roskopf J A, et al. Optimal use of older donors and recipients in kidney transplantation. Surgery. 2006; 139(3): 324-33.
14. Lee C M, Carter J T, Randall H B, Hiose R, Stock P G, Melzer J S, et al. The effect of age and prolonged cold ischemia times on the national allocation of cadaveric renal allografts. J Surg Res. 2000; 91(1): 83-8.
15. Hennige M, Kohler C O, Opelz G. Multivariate prediction model of kidney transplant success rates. Transplantation. 1986; 42(5): 491-3.
16. Su X, Zenios S A, Chertow G M. Incorporating recipient choice in kidney transplantation. J Am Soc Nephrol. 2004; 15(6): 1656-63.

We claim:

1. A method for determining a patient-specific probability of renal transplant survival, said method including:
    a) collecting clinical parameters from a plurality of patients and donor to create a training database, the clinical parameters;
    b) creating a fully unsupervised Bayesian Belief Network model using data from the training database;
    c) validating the fully unsupervised Bayesian Belief Network model;
    d) collecting the clinical parameters for an individual patient and an donor;
    e) receiving the clinical parameters for the individual patient and an donor into the fully unsupervised Bayesian Belief Network model;
    f) outputting the patient-specific probability of transplant survival from the fully unsupervised Bayesian Belief Network model to a graphical user interface for use by a clinician; and g) updating the fully unsupervised Bayesian Belief Network model using the clinical parameters for the individual patient and for the donor, and the patient-specific probability of transplant survival.

2. The method according to claim 1, wherein the patient clinical parameters include a plurality of the following: age of diabetes onset; age at time of transplant; Body Mass Index (BMI); indication of creatinine decline by 25% or more in the first 24 hours following transplant; the primary diagnosis; type of diabetes; dialysis type at time of listing; number of days on dialysis pre-transplant; an indication of return to dialysis with the first week following transplantation; length of graft survival; graft loss due to thrombosis; induction medication administered; type of transplantation procedure applied; use of maintenance or anti-rejection medications post-transplant; result of Human Leukocyte Antigen (HLA) testing; most recent serum creatinine prior to discharge following transplantation procedure; most recent absolute creatinine at time of listing; most recent Panel Reactive Antibody (PRA) in the USRDS; requirement of pretransplant dialysis; blood type; recurrent disease in graft; race; gender; serum creatinine at time of transplant; and drug treated systemic hypertension at time of listing.

3. The method according to claim 1, wherein the donor clinical parameters include: cardiac arrest since neurological event that led to declaration of brain death; total cold ischemia time; blood type; age; BMI; cause of death; serum creatinine; history of diabetes; history of hypertension; any sue of cigarettes; indication of donation after cardiac death (DCD); drug use; race; gender; organ warm ischemic time for DCD; cocaine use specifically; use of perfusion pump; and the total warm ischemia and anastomotic time.

4. The method according to claim 1, wherein said creating of the fully unsupervised Bayesian Belief Network model includes creating the fully unsupervised Bayesian Belief Network model without human-developed decision support rules.

5. The method according to claim 1, further including estimating an accuracy of the patient-specific probability of transplant survival, the accuracy including at least one of model sensitivity, model specificity, positive and negative predictive values, and overall accuracy.

* * * * *